United States Patent
Takatoku et al.

(10) Patent No.: US 8,481,016 B2
(45) Date of Patent: Jul. 9, 2013

(54) METHOD FOR INHIBITION OF POTENTIAL-DEPENDENT CATION CHANNEL

(75) Inventors: Hiroko Takatoku, Haga-gun (JP); Kentaro Kumihashi, Haga-gun (JP); Daisuke Yamazaki, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 13/643,616

(22) PCT Filed: Apr. 26, 2011

(86) PCT No.: PCT/JP2011/060110
§ 371 (c)(1),
(2), (4) Date: Oct. 26, 2012

(87) PCT Pub. No.: WO2011/142246
PCT Pub. Date: Nov. 17, 2011

(65) Prior Publication Data
US 2013/0045177 A1     Feb. 21, 2013

(30) Foreign Application Priority Data
May 12, 2010 (JP) ................. 2010-110194

(51) Int. Cl.
A61L 9/00 (2006.01)
A61L 9/01 (2006.01)

(52) U.S. Cl.
USPC ....................................... 424/76.1

(58) Field of Classification Search
None
See application file for complete search history.

(56) References Cited

U.S. PATENT DOCUMENTS

| | | | | |
|---|---|---|---|---|
| 3,649,453 | A * | 3/1972 | Herr et al. | 435/128 |
| 4,169,958 | A * | 10/1979 | Inamoto et al. | 568/665 |
| 4,985,403 | A * | 1/1991 | Narula et al. | 512/19 |
| 5,021,184 | A * | 6/1991 | Gillaspey et al. | 510/104 |
| 5,061,703 | A * | 10/1991 | Bormann et al. | 514/212.01 |
| 5,922,773 | A * | 7/1999 | Lipton et al. | 514/649 |
| 6,864,264 | B1 * | 3/2005 | Anderson et al. | 514/311 |
| 6,927,219 | B2 * | 8/2005 | Duplantier | 514/242 |
| 2003/0144293 | A1 * | 7/2003 | Duplantier | 514/242 |
| 2003/0228633 | A1 | 12/2003 | Zoller et al. | |
| 2004/0048892 | A1 * | 3/2004 | Ruppersberg et al. | 514/319 |
| 2004/0122090 | A1 | 6/2004 | Lipton | |
| 2004/0214239 | A1 | 10/2004 | Servant et al. | |
| 2005/0054650 | A1 * | 3/2005 | Ikonomidou | 514/249 |
| 2006/0134693 | A1 | 6/2006 | Servant et al. | |
| 2006/0251597 | A1 | 11/2006 | Yu et al. | |
| 2007/0037134 | A1 | 2/2007 | Servant et al. | |
| 2007/0213310 | A1 * | 9/2007 | Prokai et al. | 514/178 |
| 2011/0224095 | A1 | 9/2011 | Zoller et al. | |

FOREIGN PATENT DOCUMENTS

| | | | |
|---|---|---|---|
| EP | 1512679 A1 * | 3/2005 | |
| JP | 2002-505268 A | 2/2002 | |
| JP | 2004-515477 A | 5/2004 | |
| JP | 2005-500836 A | 1/2005 | |
| JP | 2009-084221 A | 4/2009 | |
| WO | WO 02/45710 A1 | 6/2002 | |
| WO | WO 03/004611 A2 | 1/2003 | |
| WO | WO 2006066006 A2 * | 6/2006 | |
| WO | WO 2006/119283 A2 | 11/2006 | |

OTHER PUBLICATIONS

Hiroko Takeuchi, Hirohiko Ishida, Satoshi Hikichi, and Takashi Kurahashi. Mechanism of olfactory masking in the sensory cilia. J. Gen. Physiol. vol. 133 No. 6 583-601.*

International Search Report (ISR) for PCT/JP2011/060110; I.A. fd: Apr. 26, 2011, mailed Jul. 26, 2011 from the Japanese Patent Office, Tokyo, Japan.

International Preliminary Report on Patentability (IPRP), Chapter I of the Patent Cooperation Treaty, including the Written Opinion for PCT/JP2011/060110; I.A. fd: Apr. 26, 2011, issued Dec. 10, 2012, from the International Bureau of WIPO, Geneva, Switzerland.

Kawai, F et al., "Nonselective Suppression of Voltage-gated Currents by Odorants in the Newt Olfactory Receptor Cells," J. Gen. Physiol., Feb. 1997; 109: 265-272, the Rockefeller Univ. Press, New York, NY.

Tominaga, M., "Molecular and cellular mechanisms of nociception and thermosensation," Experimental Medicine 24 (15): 54-59 (2006), Yoshida Co., Ltd., Tokyo, Japan.

Toyoda, M., "Mechanisms of itch sensation in the skin," Clinic Allround (Sogo Rinsho) 53(5): 1629-1636 (2004), Nagai Shoten, Osaka, Japan.

\* cited by examiner

*Primary Examiner* — Robert A Wax
*Assistant Examiner* — Olga V Tcherkasskaya
(74) *Attorney, Agent, or Firm* — Sterne, Kessler, Goldstein & Fox P.L.L.C.

(57) ABSTRACT

An excellent potential-dependent cation channel inhibitor or an excellent masking agent is provided. Disclosed is a method for inhibiting a potential-dependent cation channel or a method for masking olfaction, both of which include administering an adamantane derivative represented by the following formula (1) or a salt thereof [wherein $R^1$ and $R^2$ are identical with or different from each other, and each represent a hydrogen atom or an alkyl group having 1 to 6 carbon atoms; and X represents —OH, —$R^3$—OH (wherein $R^3$ represents an alkylene group having 1 to 6 carbon atoms), —$NH_2$, —$R^4$—$NH_2$ (wherein $R^4$ represents an alkylene group having 1 to 6 carbon atoms), —COOH, —$R^5$—COOH (wherein $R^5$ represents an alkylene group having 1 to 6 carbon atoms), —CO-$R^6$ (wherein $R^6$ represents an alkyl group having 1 to 6 carbon atoms), —CO—$R^7$—COO—$R^8$ (wherein $R^7$ represents an alkylene group having 1 to 6 carbon atoms, and $R^8$ represents an alkyl group having 1 to 6 carbon atoms), or —NHCO—$R^9$ (wherein $R^9$ represents an alkyl group having 1 to 6 carbon atoms)].

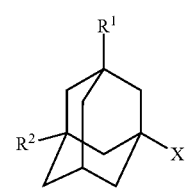

(1)

11 Claims, 3 Drawing Sheets

METHOD FOR INHIBITION OF POTENTIAL-DEPENDENT CATION CHANNEL

FIELD OF THE INVENTION

The present invention relates to a method for inhibiting a potential-dependent cation channel, and a method for masking olfaction.

BACKGROUND OF THE INVENTION

In recent years, daily discomfort caused by irritable sensation, such as an increase in hypersensitivity such as allergy due to an increase in exogenous stimulants such as chemical substances or house dust, which is caused by changes in the living environment, or a rise in the tendency of disliking foul odors of the living environment, including one's body odor and various living odors at homes, has been a problem.

Senses can be classified into somatic senses such as cutaneous sensation and deep sensation; visceral senses such as visceral pain; and special senses such as visual sensation, auditory sensation, gustatory sensation, and olfactory sensation. The sensory information is, for example, received by peripheral sensory receptors such as various receptors of the skin, muscle spindles, retina, olfactory mucosa, taste buds, and the hair cells of cochlea, converted to nerve impulses during sensory perception, and then transmitted to the sensory center as electric signals.

For example, the sensation of pain is induced by noxious stimuli (a temperature stimulus, a chemical stimulus, and a mechanical stimulus) received at the free nerve endings of the skin. In a free nerve ending, ion channels that are respectively sensitive to each of various stimuli are present, and when stimulated, these ion channels are opened, and thereby cation channels flow into the cell. Consequently, potential-dependent cation channels are activated, and an action potential (impulse) of the nerve is generated (Non-Patent Document 1). Furthermore, stimuli that are known to cause itchiness include physical stimuli such as mechanical stimuli, heat stimuli, and electrical stimuli, and chemical stimuli such as pruritogenic substances. It is speculated that these stimuli cause histamine to be released mainly from the mast cells in the dermis, and the released histamine binds to the receptors on the free nerve endings and causes an inflow of calcium ions, thereby finally generating an action potential of the nerve (Non-Patent Document 2).

Similarly, for the generation of any other sensation, the information is transmitted to the sensory center in the form of an action potential that is generated by the activation of potential-dependent cation channels of neurons. Furthermore, potential-dependent cation channels participate not only in such generation or transmission of the action potential, but also in the release of neurotransmitters at the synaptic clefts or the neuromuscular endings.

Therefore, if the activation of a potential-dependent cation channel is inhibited, sensation can be suppressed. In fact, methods for suppressing sensation by using a potential-dependent cation channel inhibitor have been traditionally used at medical sites and the like. For example, lidocaine (for example, Xylocaine (registered trademark)), which is used as a local anesthetic or an antiarrhythmic, is a potential-dependent sodium channel inhibitor. Gabapentin (for example, Gabapen (registered trademark) or Neurontin (registered trademark)), which is a potential-dependent calcium channel inhibitor, is used as an anticonvulsant or an adjuvant analgesic. Furthermore, it has been reported that an inhibitor of a potential-dependent calcium channel or a potential-dependent sodium channel (for example, Varapamil) increases the tolerance threshold of the skin against external aggression, and can be applied to hypersensitivity of the skin (Patent Document 1).

When a potential-dependent cation channel of the sensory nerves is inhibited, not only a sensory suppression effect for medical purposes may be obtained, but also there is a possibility that the quality of life can be improved by suppressing or controlling the irritable feeling or unpleasant feeling that is felt in everyday life.

Particularly, there is a demand for a masking material that can be used for the purpose of suppressing unpleasant odors of foods, pharmaceuticals, cosmetics, household commodities and the like, or for deodorization of objects.

Thus, there have been attempts to search for substances which have a strong ability to inhibit the ion channels of olfactory cells, as masking materials of unpleasant odors, by utilizing the mechanism of action of human olfactory CNG channel proteins (Patent Document 2).

However, a satisfactory masking material for unpleasant odors has not yet been obtained.

Meanwhile, adamantane derivatives have unique properties such as high heat resistance, transparency, chemical resistance, and lubricating properties, and are widely used particularly as photoresist materials. By taking advantage of these characteristics, adamantane derivatives are also used as dental compositions (Patent Document 3).

However, it is not known that adamantane derivatives have a potential-dependent channel inhibitory action or an unpleasant odor masking effect.

PRIOR ART DOCUMENTS

Patent Document
 Patent Document 1: JP-A-2002-505268
 Patent Document 2: JP-A-2005-500836
 Patent Document 3: JP-A-2009-84221
NON-PATENT DOCUMENT
 Non-Patent Document 1: Tominaga, Makoto, " Experimental Medicine", Vol. 24, No. 15:54-59 (2006)
 Non-Patent Document 2: Toyota, Masahiko, "Comprehensive Clinical", vol. 53, No. 5:1629-1636 (2004)

SUMMARY OF THE INVENTION

The present invention provides a method for inhibiting a potential-dependent cation channel, the method including administering to olfactory cells an adamantane derivative represented by the following formula (1), or a salt thereof:

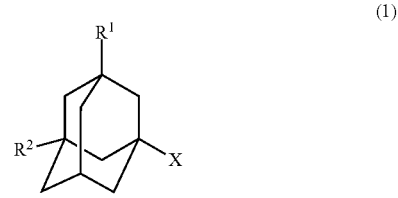

(1)

wherein $R^1$ and $R^2$ are identical with or different from each other, and each represent a hydrogen atom or an alkyl group having 1 to 6 carbon atoms; and X represents —OH, —$R^3$—OH (wherein $R^3$ represents an alkylene group having 1 to 6 carbon atoms), —$NH_2$, —$R^4$—$NH_2$ (wherein $R^4$ represents an alkylene group having 1 to 6 carbon atoms), —COON, —$R^5$—COOH (wherein $R^5$ represents an alkylene group having 1 to 6 carbon atoms), —CO—$R^6$ (wherein $R^6$ represents an alkyl group having 1 to 6 carbon atoms), —CO—$R^7$—COO—$R^8$ (wherein $R^7$ represents an alkylene group having 1 to 6 carbon atoms, and $R^8$ represents an alkyl group having 1 to 6 carbon atoms), or —NHCO—$R^9$ (wherein $R^9$ represents an alkyl group having 1 to 6 carbon atoms).

Furthermore, the present invention provides a method for masking olfaction, including administering to an animal an adamantane derivative represented by the following formula (1) or a salt thereof:

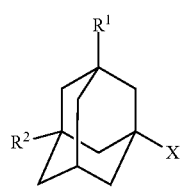

(1)

wherein $R^1$ and $R^2$ are identical with or different from each other, and each represent a hydrogen atom or an alkyl group having 1 to 6 carbon atoms; and X represents —OH, —$R^3$—OH (wherein $R^3$ represents an alkylene group having 1 to 6 carbon atoms), —$NH_2$, —$R^4$—$NH_2$ (wherein $R^4$ represents an alkylene group having 1 to 6 carbon atoms), —COOH, —$R^5$—COOH (wherein $R^5$ represents an alkylene group having 1 to 6 carbon atoms), —CO—$R^6$ (wherein $R^6$ represents an alkyl group having 1 to 6 carbon atoms), —CO—$R^7$—COO—$R^8$ (wherein $R^7$ represents an alkylene group having 1 to 6 carbon atoms, and $R^8$ represents an alkyl group having 1 to 6 carbon atoms), or —NHCO—$R^9$ (wherein $R^9$ represents an alkyl group having 1 to 6 carbon atoms), or mixing, spraying or applying the adamantane derivative represented by the above described formula (1) or a salt thereof to an object for which it is desired to reduce unpleasant odors.

DETAILED DESCRIPTION OF THE INVENTION

Figure 1:
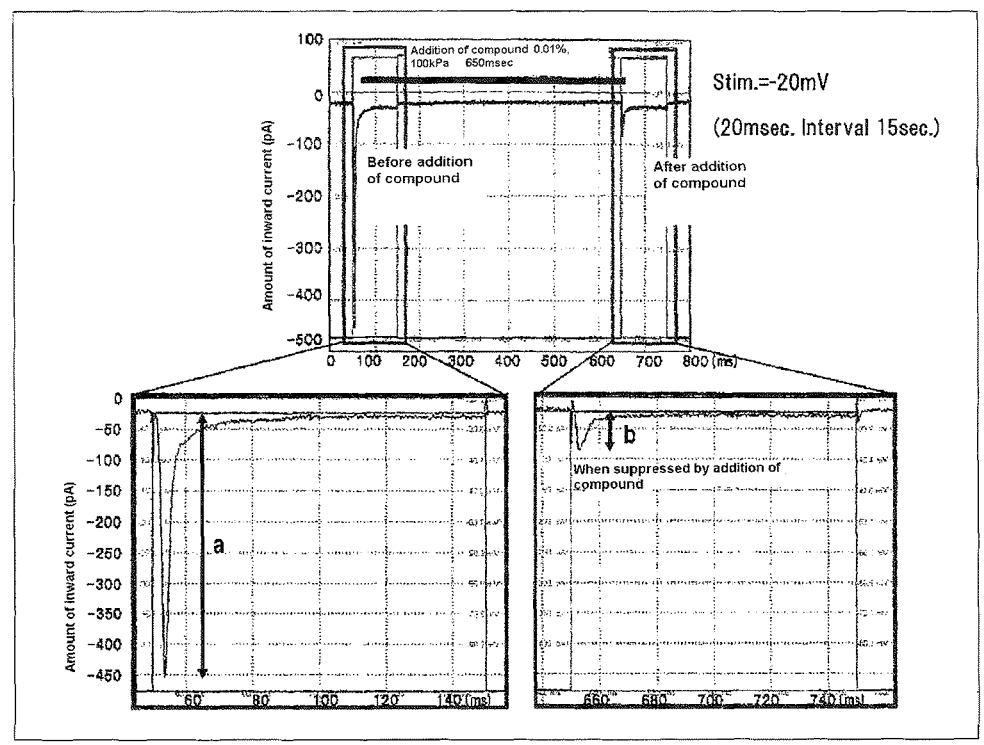
FIG. 1 shows the experimental data for the measurement of the potential-dependent cation channel activity inhibitory capacity using test substances.

The present invention relates to a method for inhibiting a potential-dependent cation channel and a masking method, which are effective for suppressing or controlling sensation, or for reducing the hypersensitive sensation or unpleasant sensation that is felt in everyday life.

The inventors of the present invention conducted a search for a substance which effectively inhibits a potential-dependent channel and can be used to suppress or control sensation, and a masking substance for unpleasant odors, and as a result, the inventors found that an adamantane derivative represented by the following formula is recognized to have an effective potential-dependent channel inhibiting effect and an effective unpleasant odor masking effect.

According to the method of the present invention, the hypersensitive sensation or unpleasant sensation that is felt in everyday life can be reduced by effectively suppressing or controlling various sensations. Furthermore, according to the present invention, unpleasant odors can be reduced. The present invention is useful in the fields of not only pharmaceutical products, but also foods, cosmetics, domestic commodities and the like, and can also be used in a wide variety of fields such as domestic commodities, pharmaceuticals and cosmetics, in which a reduction of unpleasant odors is expected.

In the method for inhibiting a potential-dependent cation channel and the method for masking olfaction of the present invention, an adamantane derivative represented by the following formula (1) is administered:

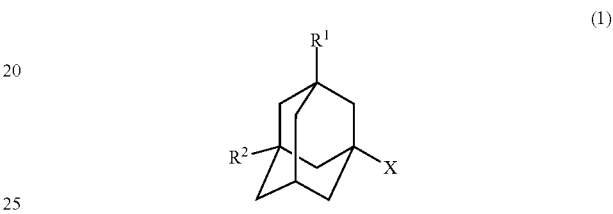

(1)

wherein $R^1$ and $R^2$ are identical with or different from each other, and each represent a hydrogen atom or an alkyl group having 1 to 6 carbon atoms; and X represents —OH, —$R^3$—OH (wherein $R^3$ represents an alkylene group having 1 to 6 carbon atoms), —$NH_2$, —$R^4$—$NH_2$ (wherein $R^4$ represents an alkylene group having 1 to 6 carbon atoms), —COOH, —$R^5$—COOH (wherein $R^5$ represents an alkylene group having 1 to 6 carbon atoms), —CO—$R^6$ (wherein $R^6$ represents an alkyl group having 1 to 6 carbon atoms), —CO—$R^7$—COO—$R^8$ (wherein $R^7$ represents an alkylene group having 1 to 6 carbon atoms, and $R^8$ represents an alkyl group having 1 to 6 carbon atoms), or NHCO—$R^9$ (wherein $R^9$ represents an alkyl group having 1 to 6 carbon atoms).

$R^1$ and $R^2$ in the formula (1) are identical with or different from each other, and each of them represents a hydrogen atom or an alkyl group having 1 to 6 carbon atoms.

Here, the alkyl groups having 1 to 6 carbon atoms represented by $R^1$ and $R^2$ include linear or branched alkyl groups, and alkyl groups having 1 to 4 carbon atoms are preferred. Examples thereof include a methyl group, an ethyl group, a propyl group, a butyl group, an isopropyl group, an isobutyl group, a sec-butyl group, and a tert-butyl group.

Among these, as $R^1$ and $R^2$ mentioned above, a hydrogen atom and a linear alkyl group are preferred; a hydrogen atom, a methyl group, an ethyl group and a propyl group are more preferred; and a hydrogen atom and a methyl group are even more preferred.

The alkylene groups having 1 to 6 carbon atoms represented by $R^3$, $R^4$, $R^5$ and $R^7$ in the formula (1) include linear or branched alkylene groups, and alkylene groups having 1 to 4 carbon atoms are preferred. Examples thereof include a methylene group, an ethylene group a methylmethylene group, an ethylmethylene group, a propylene group, a butylene group, an isopropylene group, an isobutylene group, a sec-butylene group, and a tert-butylene group. Among these, linear or branched alkylene groups having 1 to 3 carbon atoms are preferred.

Furthermore, among the alkylene groups represented by $R^3$, linear or branched alkylene groups having 1 to 2 carbon atoms are preferred, and a methylene group and an ethylene group are more preferred.

Furthermore, among the alkylene groups represented by $R^4$, linear or branched alkylene groups having 1 to 2 carbon atoms are preferred, and a methylene group and a methylmethylene group are more preferred.

Furthermore, among the alkylene groups represented by $R^5$ and $R^7$, linear or branched alkylene groups having 1 to 2 carbon atoms are preferred, and a methylene group is more preferred.

The alkyl groups having 1 to 6 carbon atoms represented by $R^6$, $R^8$ and $R^8$ in the formula (1) include linear or branched alkyl groups, and alkyl groups having 1 to 4 carbon atoms are preferred. Examples thereof include a methyl group, an ethyl group, a propyl group, a butyl group, an isopropyl group, an isobutyl group, a sec-butyl group, and a tert-butyl group. Among these, linear or branched alkyl groups having 1 to 3 carbon atoms are preferred; linear or branched alkyl groups having 1 to 2 carbon atoms are more preferred; and a methyl group and an ethyl group are even more preferred.

Here, specific examples of a compound represented by the formula (1) in which X represents —OH, include 1-adamantanol, 1-hydroxy-3-methyladamantane, 1-hydroxy-3-ethyladamantane, 1-hydroxy-3-(1-propyl)adamantane, 1-hydroxy-3-(2-propyl)adamantane, 1-hydroxy-3-(1-butyl)adamantane, 1-hydroxy-3-(2-butyl)adamantane, 1-hydroxy-3-(2-methylpropan-2-yl)adamantane, 1-hydroxy-3-vinyladamantane, 1-hydroxy-3-(2-propenyl)adamantane, 1-hydroxy-3,5-dimethyladamantane, 1-hydroxy-3-ethyl-5-methyladamantane, and 1-hydroxy-3,5-di(2-propyl)adamantane.

Furthermore, specific examples of a compound represented by the formula (1) in which X represents —$R^3$—OH, include 1-adamantane methanol, 1-adamantane ethanol, 3-(adamantan-1-yl)propan-1-ol, 2-(adamantan-1-yl)propan-1-ol, 2-(adamantan-1-yl)hexan-1-ol, (3-methyladamantan-1-yl)methanol, (3-ethyladamantan-1-yl)methanol, (3-(2-propyl)adamantan-1-yl)methanol, 2-(3-methyladamantan-1-yl)-2-propanol, 2-(3-ethyladamantan-1-yl)-2-propanol, 2-(3-(2-propyl)adamantan-1-yl)-2-propanol, 3,5-dimethyladamantane-1-methanol, 3,5-dimethyladamantane-1-ethanol, (3-methyladamantan-1-yl)methanol, 2-adamantan-1-yl-propan-2-ol, 2-(3,5-dimethyladamantan-1-yl)propan-2-ol, and 2-(3,5-diisopropyladamantan-1-yl)propan-2-ol.

Furthermore, specific examples of a compound represented by the formula (1) in which X represents —$NH_2$, include 1-adamantanamine, 1-amino-3-methyladamantane, 1-amino-3-ethyladamantane, 1-amino-3-(1-propyl)adamantane, 1-amino-3-(2-propyl)adamantane, 1-amino-3-(1-butyl)adamantane, 1-amino-3-(2-butyl)adamantane, 1-amino-3-(1-pentyl)adamantane, 1-amino-3-(1-hexyl)adamantane, and 1-aminio-3,5-dimethyladamantane. These may be in the form of salts with inorganic acids such as hydrochloric acid, or with organic acids.

Specific examples of a compound represented by the formula (1) in which X represents —$R^4$—$NH_2$, include 1-adamantane methylamine, 1-(2-aminoethyl)adamantane, 1-(adamantan-1-yl)ethylamine, 2-(adamantan-1-yl)ethylamine, 1-amino-2-(adamantan-1-yl)propane, 2-(adamantan-1-yl)-3-amino-1-propene, 1-(adamantan-1-yl)-3-amino-1-propene, 1-amino-4-(adamantan-1-yl)pentane, 1-amino-3-(adamantan-1-yl)pentane, 1-amino-3-methyl-5-(adamantan-1-yl)pentane, 1-(3-methyladamantan-1-yl) methylamine, 2-(3-methyladamantan-1-yl) ethylamine, 1-(3-ethyladamantan-1-yl) ethylamine, 1-(3,5-dimethyladamantan-1-yl)methylamine, 2-(3, 5-dimethyladamantan-1-yl) ethylamine, 1-(3, 5-dimethyladamantan-1-yl) ethylamine, 1-amino-3-(3, 5-dimethyladamantan-1-yl)propane, and 1-amino-4-(3,5-dimethyladamantan-1-yl) butane. These may be in the form of salts with inorganic acids such as hydrochloric acid, or with organic acids.

Specific examples of a compound represented by the formula (1) in which X represents —COOH or —$R^5$—COOH, include 1-adamantane acetic acid, 2-(adamantan-1-yl)butanoic acid, (3-methyladamantan-1-yl)acetic acid, (3-ethyladamantan-1-yl)acetic acid, (3-(2-propyl)adamantan-1-yl) acetic acid, (3,5-dimethyladamantan-1-yl)acetic acid, and (3,5-dimethyladamantan-1-yl)butanoic acid. These may form salts with alkali metals such as sodium and potassium.

Specific examples of a compound represented by the formula (1) in which X represents —CO—$R^6$, include 1-adamantyl methyl ketone, 1-adamantyl ethyl ketone, 1-adamantyl isopropyl ketone, 1-adamantyl t-butyl ketone, ethyl (3-isopropyladamantan-1-yl) ketone, and ethyl (3,5-dimethyladamantan-1-yl) ketone.

Specific examples of a compound represented by the formula (1) in which X represents —CO—$R^7$—COO—$R^8$, include methyl-3-(1-adamantyl)-3-oxopropionate, methyl-2,2-dimethyl-3-(1-adamantyl)-3-oxopropionate, ethyl-3-(1-adamantyl)-3-oxopropionate, and t-butyl-3-(1-adamantyl)-3-oxopropionate.

Specific examples of a compound represented by the formula (1) in which X represents —NHCO—$R^9$, include 1-acetamidoadamantane, N-(adamantan-1-yl)-propionamide, N-(adamantan-1-yl)-2-methylbutylamide, N-(3-methyladamantan-1-yl)-acetamide, N-(3-ethyladamantan-1-yl)-acetamide, N-(3-(1-propyl)-adamantan-1-yl)-acetamide, N-(3-(2-propyl)-adamantan-1-yl)-acetamide, N-(3,5-dimethyladamantan-1-yl)-acetamide, N-(3,5-diethyladamantan-1-yl)-acetamide, and N-(3,5-dimethyladamantan-1-yl)-butylamide.

X is preferably —OH, —$R^3$—OH (wherein $R^3$ represents an alkylene group having 1 to 2 carbon atoms), —$R^4$—$NH_2$ (wherein $R^4$ represents an alkylene group having 1 to 2 carbon atoms), —$R^5$—COON (wherein $R^5$ represents an alkylene group having 1 to 2 carbon atoms), —CO—$R^6$ (wherein $R^6$ represents an alkyl group having 1 to 2 carbon atoms), —CO—$R^7$—COO—$R^8$ (wherein $R^7$ represents an alkylene group having 1 to 2 carbon atoms, and $R^8$ represents an alkyl group having 1 to 2 carbon atoms), and NHCO—$R^9$ (wherein $R^9$ represents an alkyl group having 1 to 2 carbon atoms).

Among these, the compound represented by the formula (1) is preferably 1-adamantanol, 1-adamantane methanol, 1-adamantane ethanol, 3,5-dimethyladamantane-1-methanol, 1-adamantane methylamine, 1-adamantyl methyl ketone, 1-adamantane acetic acid, ethyl-3-(1-adamantyl)-3-oxopropionate, 1-acetamidoadamantane, and 1-adamantane methaneamine hydrochloride.

Furthermore, in the method for inhibiting a potential-dependent cation channel or the method for masking olfaction of the present invention, only one kind of the compound represented by the above formula (1) may be administered, or two or more kinds may also be administered in combination.

The compound represented by the formula (1) can be produced according to a known chemical synthesis method, and the compounds of the specific examples mentioned above are all known compounds.

(1) When X is —OH, the compound can be synthesized by oxidizing adamantane using an appropriate oxidizing agent such as hypochlorous acid or ozone (JP-A-2000-219646, and JP-A-2004-26778).

(2) When X is —$NH_2$, the compound can be synthesized by allowing adamantane to react with acetonitrile in the presence of fluorine and a Lewis acid to synthesize N-(1-adamantyl) acetamide, and bringing this into contact with an acid or a base (WO 01/053234).

(3) When X is —$R^3$-OH, the compound can be obtained by reducing a carboxylic acid or a carboxylic acid ester, which has a corresponding adamantyl group, using an appropriate reducing agent. For example, 1-adamantane ethanol can be synthesized by allowing 1-adamantylacetic acid to react with a borane/THF complex (Angew. Chem., 72, 628(1960)).

(4) When X is —$R^4$—$NH_2$, the compound can be synthesized by allowing an adamantane derivative having a halogen group at a corresponding alkyl group end to react with sodium azide to synthesize an azide compound, and subjecting this to a hydrogenation reaction. For example, 1-(2-aminoethyl)adamantane can be obtained by subjecting 1-(2-bromoethyl)adamantane to the action of sodium azide to synthesize 1-(2-azidoethyl)adamantane, and bringing this into contact with hydrogen in the presence of a platinum catalyst (Journal of Medicinal Chemistry, 1971, Vol. 14, No. 6, 535).

As will be disclosed in the Examples described below, since the adamantane derivative of the formula (1) or a salt thereof (hereinafter, the compound of the present invention) suppresses the electrical activity produced by the potential-dependent cation channels of biological receptor cells, in other words, since the adamantane derivative of the formula (1) or a salt thereof can suppress the generation or transmission of the action potential of nerves, that is, has a potential-dependent cation channel inhibitory action, the adamantane derivative of the formula (1) or a salt thereof can be used to suppress or control various sensations of organisms. For example, the inhibition of sodium or calcium channels of the skin peripheral nervous system can increase the tolerance threshold of the skin (Patent Document 1: JP-A-2002-505268). Also, as will described in the following Examples, the compound of the present invention is recognized to have a masking effect on unpleasant odor components. Also, as will be disclosed in the Reference Examples that will be described below, a correlation is recognized between the potential-dependent cation channel suppression ratio and the masking scores (unpleasant odors).

Here, the term "tolerance threshold of the skin" means the excitability threshold of the skin, above which value the skin exhibits, in response to the external stimuli, signs of sensory dysfunction, that is, responses accompanied by sensations with more or less pain in the skin region, for example, a pricking pain, tingling, itchiness or pruritus, burning sensation, warming sensation, discomfort, an acute pain, and/or redness or erythema.

Furthermore, the term "external stimuli" means, for example, irritable compounds such as surfactants, antiseptics, or fragrances, and environments, foods, wind, friction, shaving, soaps, hard water with high calcium concentrations, temperature changes, woolen yarn, and the like.

Here, the potential-dependent cation channel inhibition according to the present invention means that the inflow of ions into the cells through a potential-dependent cation channel is inhibited. Examples of the potential-dependent cation channel that is inhibited in the present invention include potential-dependent $Na^+$ channels, potential-dependent $K^+$ channels, and potential-dependent $Ca^{2+}$ channels. Among these, the potential-dependent $Ca^{2+}$ channels can be further classified into L-type, N-type, P-type, Q-type, R-type, and T-type, on the basis of electrophysiological and pharmacological properties, and these are all targets of the compound of the present invention.

Furthermore, examples of the various sensations to be suppressed or controlled include the somatic senses including the tactile sensation, the sense of pressure, the sense of heat, the sense of coldness, and the sensation of pain received through the skin or mucosa, as well as the sensations from muscles, tendons and joints; visceral senses including the organic sensation and visceral pain; special senses such as visual sensation, auditory sensation, gustatory sensation, olfactory sensation and a sense of balance; and other sensations (for example, itchy sensation, numbness, neuralgia, pain, and other discomforts). All of these sensations can be suppressed, alleviated or ameliorated by a potential-dependent cation inhibitory substance. Furthermore, these various sensations are such that the sensitivity to stimulation is frequently accentuated, and unpleasant symptoms called skin hyperesthesia, such as olfactory hyperesthesia, hyperalgesia, allodynia, and hypersensitive itching are exhibited. However, among these symptoms, inhibition of the potential-dependent cation channels can be utilized in the prevention, improvement or treatment of symptoms attributable to the accentuation of peripheral sensory nerve activities.

Meanwhile, hyperalgesia means paresthesia in which the sensation of pain is accentuated, and the stimulus that causes pain is more strongly felt, and allodynia means paresthesia in which even those stimuli that do not cause pains in ordinary cases are all recognized as pains. Hypersensitive itching means paresthesia in which itchiness is felt even under a stimulus that does not cause itchiness in ordinary cases.

Therefore, the compound of the present invention can be used to promote the inhibition of a potential-dependent cation channel, an improvement of skin hyperesthesia, and olfaction masking, by ingesting or administering the compound to an animal, including a human being, or by mixing, spraying or applying the compound to an object for which it is desired to reduce unpleasant odors. Furthermore, the compound of the present invention can serve as a potential-dependent cation channel inhibitor, a skin hyperesthesia ameliorating agent, and an olfaction masking agent (hereinafter, also referred to as "potential-dependent cation channel inhibitor and the like"), and can also be used to produce such potential-dependent cation channel inhibitor and the like.

Therefore, the compound of the present invention is useful as a pharmaceutical product, a quasi-pharmaceutical product, a cosmetic product, a house care product, a food product, a functional food product, an animal feed, or the like, for the inhibition of a potential-dependent cation channel, the amelioration of hyperesthesia, or masking, or is useful as a material or a preparation to be incorporated into these pharmaceutical products and the like.

Examples of the pharmaceutical product, quasi-pharmaceutical product, other compositions or the like include pharmaceutical products and quasi-pharmaceutical products, such as an anesthetic, a sedative, an analgesic, an antitussive, an anti-inflammatory agent, a suppressant of excessive sensation such as hypersensitivity or allergic reactions, an antipruritic, and drugs for pain clinic, which are used in the field of medicine or veterinary medicine, and an olfaction inhibitor based on inhalation or nasal drop, which is used in nursing or travel; house care products such as an antifungal agent, a liquid type antibacterial finishing agent for clothing, a detergent for clothing, a softener for clothing, a bleaching agent for clothing, a household detergent, a drain cleaner, a bathroom detergent, a toilet detergent, an aromatizing or deodorizing cleaner for toilet, a detergent for washing machines, a kitchen cleaner, a dishwashing cleaner, and a deodorizer; and body care products such as a bathing powder or a cosmetic material, which has a skin hypersensitivity suppressive action, a toothpaste powder, a mouse washer or the like, which has a hyperesthesia suppressive action, wet tissues, an antiperspirant, and wiping sheets.

The pharmaceutical products and quasi-pharmaceutical products containing the compound of the present invention can be administered in an arbitrary dosage form, in accordance with the target sensation or the target object or body part. Examples of the target sensation are as described above, while examples of the target object or body part include a biological organism, and biological tissues, organs and cells.

The dosage form may be of orally administered type and of parenterally administered type. Examples of formulations for oral administration include solid dosage forms such as tablets, coated tablets, granules, powders, and capsules; and liquid dosage forms such as elixirs, syrups, and suspensions. Examples of routes for parenteral administration include injection, infusion, transdermal, transmucosal, transnasal, enteral, inhalation, suppositories, and boluses, and examples of formulations include tablets, capsules, liquids, powders, granules, ointments, sprays, mist, creams, emulsions, gels, pastes, lotions, patches, plasters, sticks, and sheets.

In the preparations described above, the compound of the present invention may be used in combination with other optional components as necessary. Preferred examples of the other components include pharmaceutically acceptable carriers. Specific examples of the pharmaceutically acceptable carriers include an excipient, a binder, a disintegrant, a lubricating agent, a diluent, an osmotic pressure regulating agent, a pH adjusting agent, an emulsifier, an antiseptic, a stabilizer, an antioxidant, a colorant, an ultraviolet absorber, a moisturizer, a thickener, a glazing agent, an activity enhancing agent, a savoring agent, and a flavoring agent. The potential-dependent cation channel inhibitor of the present invention may also be used in further combination with other known efficacious components (for example, another ion channel inhibitor, a sensation suppressing or controlling agent, an anti-inflammatory agent, and a disinfectant).

The incorporation amount of the compound of the present invention in the pharmaceutical products, quasi-pharmaceutical products, other compositions and the like may vary with the form of use or the purpose, but for example, in the case of using the compound for the suppression of sensation, the incorporation amount is usually from 0.01% to 50% by mass, preferably from 0.1% to 10% by mass, and more preferably from 0.1% to 5% by mass.

Examples of food products and animal feeds containing the compound of the present invention include food products such as breads and buns, noodles, confectionery, jellies, dairy products, frozen foods, instant foods, starch processing products, processed meat products, other processed food products, beverages, soups, seasonings and nutritional supplementary foods; and animal feeds, such as fodders for livestock used for cattle, pig, chicken, sheep and horses, feeds for small animals used for rabbit, rat and mouse, feeds for fishes used for tuna, eel, sea bream, yellowtail and shrimp, and pet foods used for dog, cat, small birds and squirrel.

In the food products and animal feeds, the compound of the present invention may be used in combination with other optional components as necessary. Preferred examples of the other components include carriers acceptable in the fields of food products and animal feeds. Specific examples of the acceptable carriers include a solvent, a softening agent, fats and oils, an emulsifier, an antiseptic, a flavor, a stabilizer, a colorant, an ultraviolet absorber, an antioxidant, a moisturizer, a thickener, a gelling agent, a shape retaining agent, a pH adjusting agent, a seasoning, an antiseptic, and a nutrition reinforcing agent.

There are no particular limitations on the form of the food products and animal feeds, but liquid forms, semisolid forms, and solid forms, as well as forms such as tablets, pills, capsules, liquids, syrups, powders and granules, which are similar to the orally administered preparations described above may be used.

Furthermore, the content of the compound of the present invention in the food products or animal feeds may vary with the form of use, but the content in terms of dried product is usually 0.001% to 50% by mass, preferably 0.01% to 10% by mass, and more preferably 0.1% to 5% by mass.

The amount of administration/intake in the case of using the compound of the present invention as a pharmaceutical product or a functional food product, or by incorporating the compound into these products, is not particularly limited as long as it is an efficacious amount. Furthermore, the amount of administration/intake may vary depending on the condition, body weight, gender and age of the subject, or other factors, but the amount of administration/intake per day of an adult in the case of oral administration/intake is usually preferably 0.001 g to 100 g in terms of the compound of the present invention. Also, the preparations described above can be administered or taken in according to an arbitrary administration/intake plan, but it is preferable to administer or take in once or several times in a day, continuously for several weeks to several months.

The subject of administration or intake of the compound of the present invention in connection with the method of the present invention is not particularly limited as long as the object needs the administration or intake. However, a human being or a mammal other than human being, who/which is intended to suppress or control the various sensations described above, for example, intended for the amelioration of skin hyperesthesia or olfaction masking, is preferred.

EXAMPLES

Hereinafter, the present invention will be specifically described by way of Examples and Test Examples, but the present invention is not intended to be limited to these Examples.

[Test Substance: Adamantane and Derivatives Thereof]

As indicated in Table 1, for all of adamantane, 1,3-dimethyladamantane, 1-adamantanol, 1-adamantane methanol, 1-adamantane ethanol, 3,5-dimethyladamantane-1-methanol, 1-adamantane methylamine, 1-adamantyl methyl ketone, 1-adamantane acetic acid, ethyl-3-(1-adamantyl)-3-oxopropionate, 1-acetamidoadamantane and 1-adamantane methaneamine hydrochloride, products purchased from Sigma-Aldrich Japan were used.

Test Example 1: Test for Measuring Potential-Dependent Cation Channel Activity

1. Isolation of Olfactory Cells

Olfactory cells were isolated from a Japanese fire belly newt (Cynops pyrrhogaster) according to a known method (Kurahashi, et al., J. Physiol. (1989), Vol. 419:177-192), and the olfactory cells were immersed in a normal Ringer's solution. To briefly explain the method of isolation, each newt which had been hibernated in ice-water was double-pithed, and the cranium was cut open to remove olfactory mucosa. The removed olfactory mucosa was incubated in a 0.1% collagenase solution at 37° C. for 5 minutes, and collagenase was washed off. Subsequently, the mucosal tissue was crushed by means of a glass pipette to thereby isolate cells. As the normal Ringer's solution, a solution of 110 mM NaCl, 3.7 mM KCl, 3 mM $CaCl_2$, 1 mM $MgCl_2$, 15 mM glucose, 1 mM sodium pyruvate, 10 mM HEPES, and 0.001% (w/v) Phenol Red, at pH 7.4 (adjusted with NaOH), was used.

2. Measurement of Electrical Activity [A. Setting] The membrane potential of the isolated olfactory cells was fixed by a whole-cell recording method, and the membrane current was measured (Kawai, et al., J. Gen. Physiol. (1997), Vol. 10:265-272). A borosilicate glass capillary (diameter: 1.2 mm) was used as the electrode, and the electrode was produced using a puller for electrode fabrication (P-97, Sutter Instrument Co.) (electrode resistance: approximately 6.0 MΩ). An electrode filling solution and a silver-silver chloride wire were inserted into the electrode, the silver-silver chloride wire was connected to a patch clamp amplifier (EPC10, HEKA), and thus fixation of the membrane potential and depolarization simulation were performed. As the electrode filling solution, a solution of 119 mM CsCl, 10 mM HEPES, 1 mM $CaCl_2$, 5 mM EGTA, and 0.0010 (w/v) Phenol Red at pH 7.4 (adjusted with CsOH), was used. The recording of the membrane current was performed using a computer (IBM-compatible) connected to the patch clamp amplifier (sampling frequency: 1 kHz), and Patch Master software (HEKA) was used for the measurement and analysis. The addition (spraying) of a test substance was carried out using a pressure controller. A pressure controller is a an apparatus which reduces the pressure of compressed air supplied by an air compressor to any pressure under computer-controlled conditions, and sends the compressed air to the tail of a glass pipette filled with a test substance for a predetermined time period (Ito, et al., Nippon Seirigaku Zasshi (Journal of the Physiological Society of Japan), 1995, vol. 57, 127-133).

[B. Procedure] In order to investigate the effect of each of the test substances described above (see Table 1) on the potential-dependent cation channel activity, the membrane potential of the isolated olfactory cells was fixed at –90 mV, and the membrane potential was depolarized to –20 mV for 20 milliseconds at an interval of 200 milliseconds. The peak intensity of the inward current produced immediately after depolarization (FIG. 1. |a|=[Inward current value produced immediately after depolarization]–[baseline value]) was measured. While depolarization stimulation was continuously repeated, the test substance was adjusted to the various concentrations indicated in Table 1 using normal Ringer's solution, and the mixture was added to the olfactory cells by spraying the mixture (for 650 milliseconds, pressure: 100 kPa) through a glass pipette (tip diameter: 1 μm) that was placed such that the tip of the pipette was located in the vicinity (10 μm) of the olfactory cells. The change in the inward current (FIG. 1, |b|=[Inward current value when the peak intensity was most suppressed]–[baseline value]) resulting from the spraying was investigated. This spraying was carried out continuous for 5 times. Furthermore, the average value A of the peak intensities (a) of the inward current produced by the depolarization immediately before the addition of an extract, and the average value B of the peak intensities (b) of the inward current produced by the depolarization immediately after the addition of an extract were calculated.

Furthermore, during the test, there are very rare occasions in which upon the addition of a test substance, the olfactory receptor responds to the test substance, and an inward current originating from CNG channels is observed; however, such a case was excluded. It can be speculated that this occurs when the test substance acts as an agonist to the olfactory receptor on the olfactory cells used in the test. The CNG channel current can be easily distinguished from the potential-dependent channel current, in terms of the intensity, peak shape, duration and the like.

The "inward current suppression ratio (%)" was calculated from the "B: average value of the inward current value (b) when the peak intensity was most suppressed" and the "A: average value of the inward current value (a) produced immediately after the depolarization immediately before the addition of an extract," as shown in the following formula. Based on these results, the suppression capacity on the electrical activity of the potential-dependent cation channel caused by the addition of each test substance was evaluated, and the inward current suppression ratios of the various test substances are presented in Table 1. Meanwhile, a higher inward current suppression ratio means that the potential-dependent cation channel inhibitory effect is higher.

Inward current suppression ratio (%)=[1−(A/B)]×100

The results of the above test are presented in Table 1.

TABLE 1

| | Compound name | Structural formula | Evaluation concentration | Inhibition ratio (%) |
|---|---|---|---|---|
| Comparative Example 1 | Adamantane | (adamantane structure) | 0.04% | 10.9 |
| Comparative Example 2 | 1,3-Dimethyladamantane | (1,3-dimethyladamantane structure) | 0.01% | 0 |
| Example 1 | 1-Adamantanol | (1-adamantanol structure) | 0.04% | 72.4 |

TABLE 1-continued

| | Compound name | Structural formula | Evaluation concentration | Inhibition ratio (%) |
|---|---|---|---|---|
| Example 2 | 1-Adamantane ethanol | | 0.04% | 63.4 |
| Example 3 | 1-Adamantane methanol | | 0.04% | 99 |
| Example 4 | 1-Adamantane methanol | | 0.01% | 70 |
| Example 5 | 3,5-Dimethyladamantane-1-methanol | | 0.01% | 59.9 |
| Example 6 | 1-Adamantane methylamine | | 0.01% | 54.5 |
| Example 7 | 1-Adamantylmethyl ketone | | 0.01% | 32 |
| Example 8 | 1-Adamantane acetic acid | | 0.04% | 82.5 |
| Example 9 | Ethyl-3-(1-adamantyl)-3-oxopropionate | | 0.01% | 45.5 |
| Example 10 | 1-Acetamidoadamantane | | 0.01% | 40.6 |

TABLE 1-continued

| | Compound name | Structural formula | Evaluation concentration | Inhibition ratio (%) |
|---|---|---|---|---|
| Example 11 | 1-Adamantane methaneamine hydrochloride | | 0.01% | 78.9 |

Test Example 2: Olfaction Masking Test

An olfaction masking test based on sensory evaluation was carried out with 10 panelists. Hexanoic acid (10%) was used as a malodorous substance, and 20 μL of the malodorous substance and 20 μL of a test solution of an adamantane derivative at a concentration of 50% (1-adamantane acetic acid at a concentration of 25%) were impregnated into the same cotton ball (diameter: 1 cm). The cotton ball was placed in a 50-mL container, and the malodorous substance was volatilized overnight at room temperature.

The evaluation was carried out such that each panelist smelled the odor in the container, and determined the strength of masking of hexanoic acid by the addition of the adamantane derivatives. The intensity of odor of simple hexanoic acid was set to 5.0, which is an intermediate point among the 21 grades of evaluation criteria (0: no odor, 10: strong odor).

[Results]

Figure 2:
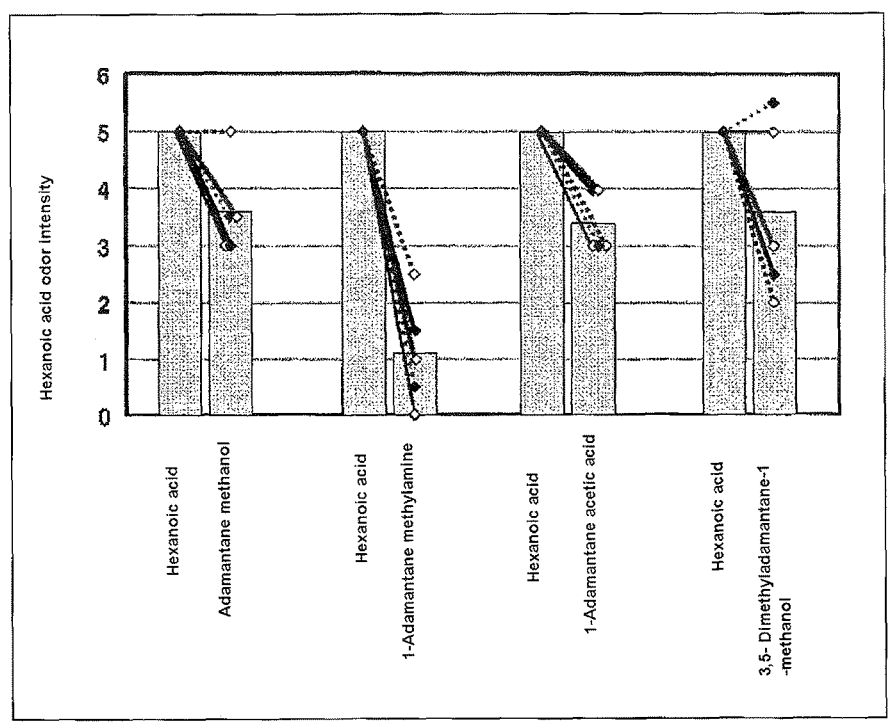
FIG. 2 shows the test results for the masking of unpleasant odor components by 1-adamantane methanol, 1-adamantane methylamine, 1-adamantane acetic acid, and 3,5-dimethyladamantane-1-methanol in human beings.

Changes in the intensity of odor relative to simple hexanoic acid are presented in FIG. 2, and the odor intensity suppression ratios are presented in Table 2. An olfaction masking effect was recognized as a result of the addition of various adamantane derivatives.

TABLE 2

| Hexanoic acid odor intensity suppression ratio (%) | |
|---|---|
| 1-Adamantane methanol | 28 |
| 1-Adamantane methylamine | 78 |
| 1-Adamantane acetic acid | 32 |
| 3,5-Dimethyladamantane-1-methanol | 28 |

Figure 3:
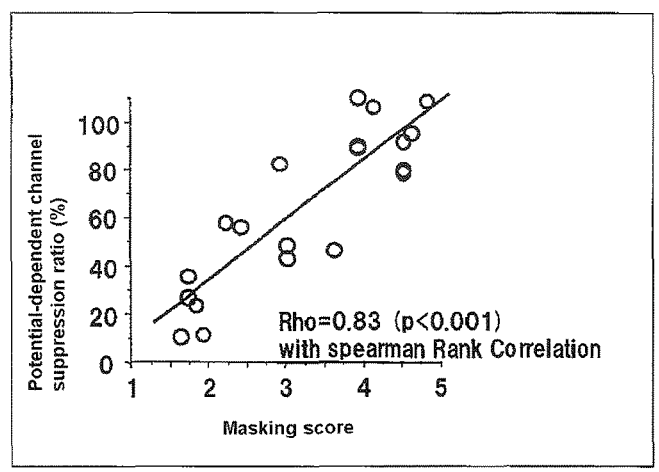
FIG. 3 shows the correlation between the potential-dependent cation channel inhibitory activity ratio and the masking scores.

Reference Example: Correlation between potential-dependent channel inhibitory action and masking effect As shown in FIG. 3 and Table 3, a correlation between the inward current suppression ratio (%) and the masking score was recognized from the results obtained by using various samples. Therefore, components having a potential-dependent cation channel inhibitory action are useful as masking materials for unpleasant odors.

[Sensory evaluation test]

An olfaction masking test based on sensory evaluation was carried out with 20 panelists. Isovaleric acid (1%) was used as a malodorous substance, and 1,8-cineol which is known to have an olfaction sensitivity inhibitory effect against foul odors was used as a control.

2 μL of the malodorous substance and 4 μL of a test solution of each of the test compounds indicated in Table 3 at a concentration of 0.1% were impregnated into separate cotton balls (diameter: 1 cm), and the substances were volatilized for 12 hours at room temperature in each of separate 50-mL injection syringes. The isovaleric acid and test compound volatilized in the syringe were injected into a PP container (capacity: 500 mL) with a cap and were mixed in the container.

The evaluation was carried out such that each panelist slightly opened the cap of the PP container and smelled the odor in the container, and the panelist determined the masking strength for the odor of isovaleric acid.

The evaluation of the masking strength was carried out based on the following six-grade masking scores, based on a comparison with the intensity of odor in a PP container to which only volatilized isovaleric acid had been injected. These results are presented in Table 3.

0: Masking is not achieved.
1: A very slight masking effect is recognized.
2: A slight masking effect is recognized.
3: A sufficient masking effect is recognized.
4: Masking is almost achieved.
5: Perfect masking is achieved.

TABLE 3

| | Fragrance name | Masking score | Channel suppression ratio |
|---|---|---|---|
| 1 | DIHYDRO MYRCENOL | 4.8 | 109.0 |
| 2 | LYRAL | 1.7 | 35.7 |
| 3 | POIRENATE | 3 | 48.7 |
| 4 | AMBER CORE | 1.7 | 27.1 |
| 5 | o-t-B.C.H.A | 1.8 | 23.8 |
| 6 | b-DAMASCONE | 2.4 | 56.1 |
| 7 | PHENYL ETHYL ALCOHOL | 2.9 | 82.6 |
| 8 | iso-AMYL ACETATE | 4.5 | 92.0 |
| 9 | TRIPLAL | 4.5 | 79.9 |
| 10 | CIT RAL | 3.9 | 110.6 |
| 11 | FRUIT ATE | 1.9 | 11.6 |
| 12 | BENZALDEHYDE | 4.6 | 95.4 |
| 13 | cis-3-HEXENOL | 4.5 | 78.7 |
| 14 | 1,8-Cineol | 3.6 | 46.5 |
| 15 | Linalool | 4.1 | 106.5 |
| 16 | BENTHYL BENZOATE | 1.6 | 10.7 |
| 17 | LILIAL | 2.2 | 57.9 |
| 18 | ANIS ALDEHYDE | 3.9 | 89.3 |
| 19 | LINALYL ACETATE | 3 | 43.3 |
| 20 | GERANIOL | 3.9 | 90.1 |

The invention claimed is:
1. A method for inhibiting a potential-dependent cation channel, the method comprising administering to olfactory cells an adamantane derivative represented by the following formula (1) or a salt thereof:

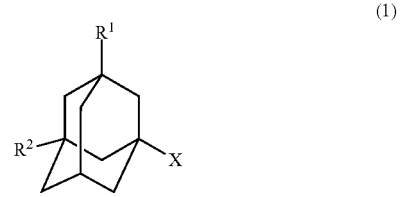

wherein $R^1$ and $R^2$ are identical with or different from each other, and each represent a hydrogen atom or an alkyl group having 1 to 6 carbon atoms; and X represents —OH, —$R^3$—OH (wherein $R^3$ represents an alkylene group having 1 to 6 carbon atoms), —$NH_2$, —$R^4$—$NH_2$ (wherein $R^4$ represents an alkylene group having 1 to 6 carbon atoms), —COOH, —$R^5$—COOH (wherein $R^5$ represents an alkylene group having 1 to 6 carbon atoms), —CO—$R^6$ (wherein $R^6$ represents an alkyl group having 1 to 6 carbon atoms), —CO—$R^7$—COO—$R^8$ (wherein $R^7$ represents an alkylene group having 1 to 6 carbon atoms, and $R^8$ represents an alkyl group having 1 to 6 carbon atoms), or —NHCO—$R^9$ (wherein $R^9$ represents an alkyl group having 1 to 6 carbon atoms).

2. The method according to claim 1, wherein $R^1$ and $R^2$ are identical with or different from each other, and $R^1$ and $R^2$ each represent a hydrogen atom or a methyl group.

3. The method according to claim 1, wherein $R^3$, $R^4$, $R^5$ and $R^7$ each represent an alkylene group having 1 to 4 carbon atoms, and $R^6$, $R^8$ and $R^9$ each represent an alkyl group having 1 to 4 carbon atoms.

4. The method according to claim 1, wherein X represents —OH, —$R^3$—OH (wherein $R^3$ represents an alkylene group having 1 to 2 carbon atoms), —$R^4$—$NH_2$ (wherein $R^4$ represents an alkylene group having 1 to 2 carbon atoms), —$R^5$—COOH (wherein $R^5$ represents an alkylene group having 1 to 2 carbon atoms), —CO—$R^6$ (wherein $R^6$ represents an alkyl group having 1 to 2 carbon atoms), —CO—$R^7$—COO—$R^8$ (wherein $R^7$ represents an alkylene group having 1 to 2 carbon atoms, and $R^8$ represents an alkyl group having 1 to 2 carbon atoms), or NHCO—$R^9$ (wherein $R^9$ represents an alkyl group having 1 to 2 carbon atoms).

5. The method according to claim 1, wherein the compound represented by the formula (1) is 1-adamantanol, 1-adamantane methanol, 1-adamantane ethanol,
3,5-dimethyladamantane-1-methanol, 1-adamantane methylamine, 1-adamantyl methyl ketone, 1-adamantane acetic acid, ethyl-3-(1-adamantyl)-3-oxopropionate,
1-acetamidoadamantane, or 1-adamantane methaneamine hydrochloride.

6. The method according to claim 1, wherein a subject for the administration is an animal.

7. A method for masking olfaction, the method comprising administering to an animal an adamantane derivative represented by the following formula (1) or a salt thereof:

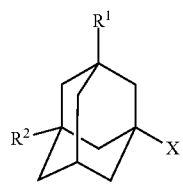

(1)

wherein $R^1$ and $R^2$ are identical with or different from each other, and each represent a hydrogen atom or an alkyl group having 1 to 6 carbon atoms; and X represents —OH, —$R^3$—OH (wherein $R^3$ represents an alkylene group having 1 to 6 carbon atoms), —$NH_2$, —$R^4$—$NH_2$ (wherein $R^4$ represents an alkylene group having 1 to 6 carbon atoms), —COOH, —$R^5$—COOH (wherein $R^5$ represents an alkylene group having 1 to 6 carbon atoms), —CO—$R^6$ (wherein $R^6$ represents an alkyl group having 1 to 6 carbon atoms), —CO—$R^7$—COO—$R^8$ (wherein $R^7$ represents an alkylene group having 1 to 6 carbon atoms, and $R^8$ represents an alkyl group having 1 to 6 carbon atoms), or —NHCO—$R^9$ (wherein $R^9$ represents an alkyl group having 1 to 6 carbon atoms), or mixing, spraying or applying the adamantane derivative or a salt thereof to an object for which it is desired to reduce an unpleasant odor.

8. The method according to claim 7, wherein $R^1$ and $R^2$ are identical with or different from each other, and $R^1$ and $R^2$ each represent a hydrogen atom or a methyl group.

9. The method according to claim 7, wherein $R^3$, $R^4$, $R^5$ and $R^7$ each represent an alkylene group having 1 to 4 carbon atoms, and $R^6$, $R^8$ and $R^9$ each represent an alkyl group having 1 to 4 carbon atoms.

10. The method according to claim 7, wherein X represents —OH, —$R^3$—OH (wherein $R^3$ represents an alkylene group having 1 to 2 carbon atoms), —$R^4$—$NH_2$ (wherein $R^4$ represents an alkylene group having 1 to 2 carbon atoms), —$R^5$—COOH (wherein $R^5$ represents an alkylene group having 1 to 2 carbon atoms), —CO—$R^6$ (wherein $R^6$ represents an alkyl group having 1 to 2 carbon atoms), —CO—$R^7$—COO—$R^8$ (wherein $R^7$ represents an alkylene group having 1 to 2 carbon atoms, and $R^8$ represents an alkyl group having 1 to 2 carbon atoms), and NHCO—$R^9$ (wherein $R^9$ represents an alkyl group having 1 to 2 carbon atoms).

11. The method according to claim 7, wherein the compound represented by the formula (1) is 1-adamantanol, 1-adamantane methanol, 1-adamantane ethanol,
3,5-dimethyladamantane-1-methanol, 1-adamantane methylamine, 1-adamantyl methyl ketone, 1-adamantane acetic acid, ethyl-3-(1-adamantyl)-3-oxopropionate,
1-acetamidoadamantane, or 1-adamantane methaneamine hydrochloride.

* * * * *